(12) United States Patent
Foo et al.

(10) Patent No.: US 9,480,721 B2
(45) Date of Patent: Nov. 1, 2016

(54) TUMOUR CYTOTOXIC AGENT AND METHODS THEREOF

(75) Inventors: Hooi Ling Foo, Selangor (MY); Teck Chwen Loh, Selangor (MY); Li Oon Chuah, Selangor (MY); Noorjahan Banu Alitheen, Selangor (MY); Raha Abdul Rahim, Selangor (MY)

(73) Assignee: UNIVERSITI PUTRA MALAYSIA, Selangor (MY)

( * ) Notice: Subject to any disclaimer, the term of this patent is extended or adjusted under 35 U.S.C. 154(b) by 522 days.

(21) Appl. No.: 13/579,936

(22) PCT Filed: Nov. 29, 2010

(86) PCT No.: PCT/MY2010/000307
§ 371 (c)(1),
(2), (4) Date: Aug. 20, 2013

(87) PCT Pub. No.: WO2012/074351
PCT Pub. Date: Jun. 7, 2012

(65) Prior Publication Data
US 2013/0323215 A1   Dec. 5, 2013

(51) Int. Cl.
| | |
|---|---|
| *C12N 1/20* | (2006.01) |
| *C12R 1/25* | (2006.01) |
| *A61K 35/74* | (2015.01) |
| *A61K 35/747* | (2015.01) |
| *A23L 1/30* | (2006.01) |
| *A61K 38/16* | (2006.01) |

(52) U.S. Cl.
CPC .............. *A61K 35/74* (2013.01); *A23L 1/3014* (2013.01); *A61K 35/747* (2013.01); *A61K 38/164* (2013.01); *C12N 1/20* (2013.01); *C12R 1/25* (2013.01); *A23V 2002/00* (2013.01); *A23Y 2220/67* (2013.01)

(58) Field of Classification Search
None
See application file for complete search history.

(56) References Cited

FOREIGN PATENT DOCUMENTS

| WO | WO 2010/117255 A1 | 10/2010 |
| WO | WO 2011/019264 A1 | 2/2011 |

OTHER PUBLICATIONS

Herbs4U's Blog, Tapai Ubi or Fermented Tapioca, Mar. 29, 2009.*
Murosaki et al., Antitumor effect of heat-killed *Lactobacillus plantarum* L-137 through restoration of impaired interleuking-12 production in tumor-bearing mice, Cancer Immunol Immunother (2000) 49:157-164.*
Foo, H. L. et al., "Effects of Adding *Lactobacillus plantarum* I-UL4 Metabolites in Drinking Water of Rats," *Pakistan Journal of Nutrition*, 2003, vol. 2, No. 5, pp. 283-288.
Foo, H. L. et al., "Effects of Feeding *Lactobacillus plantarum* I-UL4 Isolated from Malaysian Tempeh on Grownth Performance, Faecal Flora and Lactic Acid Bacteria and Plasma Cholesterol Concentrations in Postweaning Rats," *Food Science and Biotechnology*, 2003, vol. 12, No. 4, pp. 403-408.
Thu, T. V. et al., "Effects of liquid metabolite combinations produced by *Lactobacillus plantarum* on growth performance, faeces characteristics, intestinal morphology and diarrhoea incidence in postweaning piglets," *Tropical Animal Health and Production*, Jul. 2010, vol. 43, No. 1, pp. 69-75.

* cited by examiner

*Primary Examiner* — Suzanne M Noakes
*Assistant Examiner* — Stephen Chong
(74) *Attorney, Agent, or Firm* — Saliwanchik, Lloyd & Eisenschenk

(57) ABSTRACT

The present invention discloses a novel antitumor agent which provides an antitumor activity based on metabolites with reduced side effects. Moreover, the antitumor agent is prepared starting with a highly safe bacterium used in food production, which is a probiotic lactic acid bacterium.

23 Claims, 10 Drawing Sheets

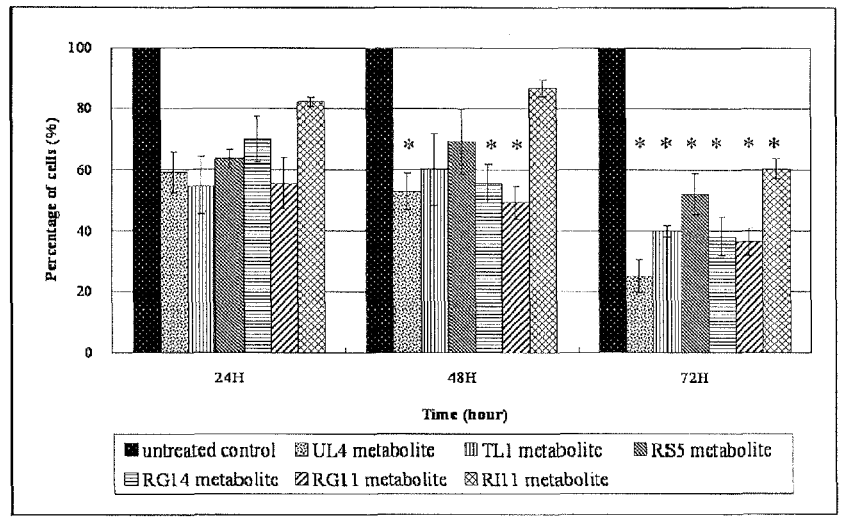
FIGURE 1: Anti-proliferative effect of metabolites derived from six strains of Lactic acid bacteria on MCF-7 cells.
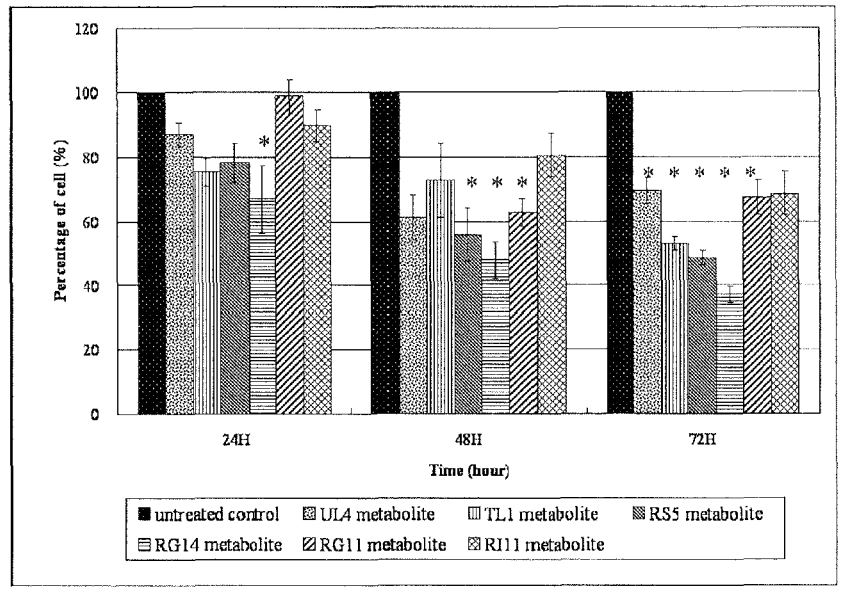
FIGURE 2: Anti-proliferative effect of metabolites derived from six strains of Lactic acid bacteria on HT-29 cells.

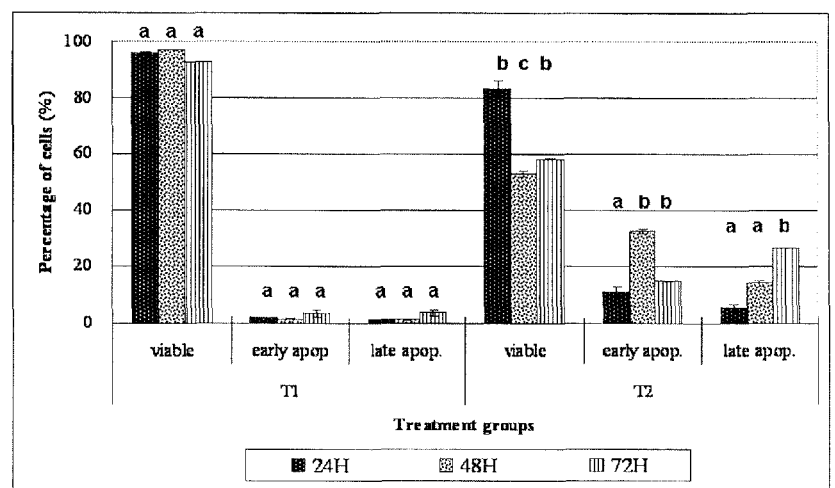
FIGURE 3: Apoptosis induction of Lactic acid bacteria metabolites on MCF-7 cells.

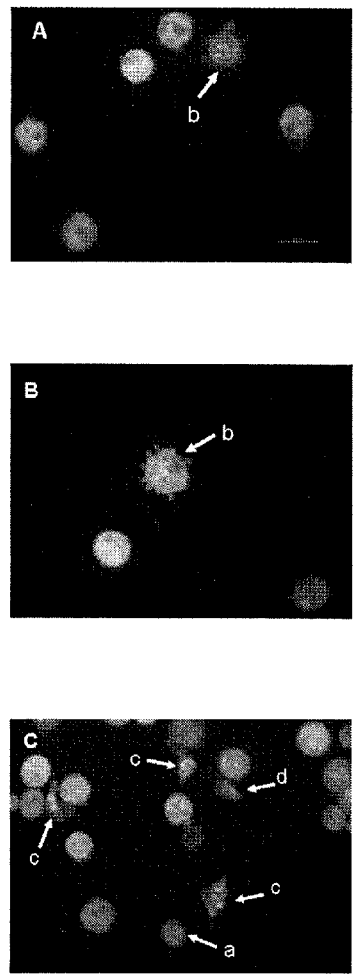
FIGURE 4: Fluorescence photomicrographs of MCF-7 cells treated with UL4 metabolite. Panel A: 24 hours, B: 48 hours and C: 72 hours. Morphological changes following exposure to LAB metabolite are typical of apoptosis, showing ↑a = cell shrinkage, ↑b = membrane blebbing, ↑c = apoptotic bodies formation, and ↑d, necrotic cells. (Magnification: 400 ×).

A

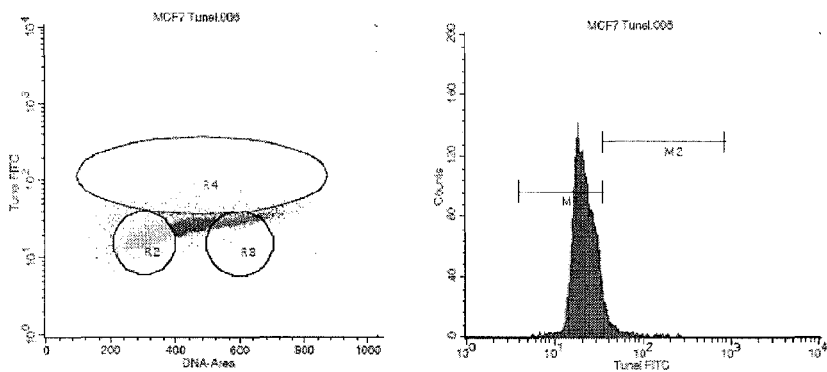

B

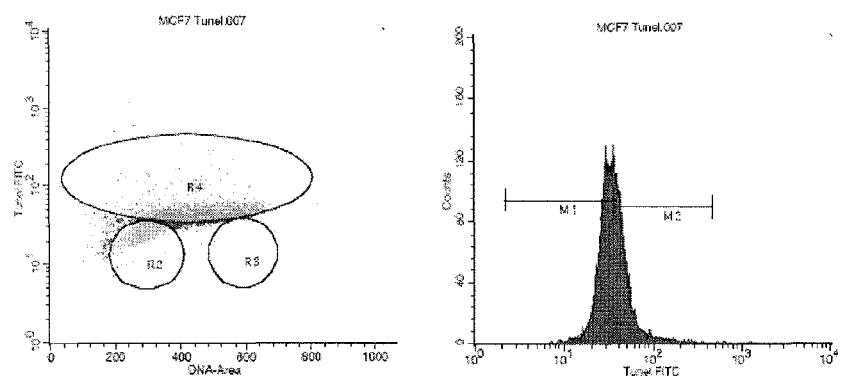

FIGURE 5: Two-parameter scatterplots (left panel) and single parameter histogram (right panel) illustrating the detection of DNA strand breaks in apoptotic cells by TUNEL assay. Panel A: 72h untreated control; B: 72h treated with UL4 metabolite. Apoptotic cells (R4) are characterized by very high frequency of DNA strand breaks (note exponential scale of Y coordinate) in scatterplots and M2 gate in histogram.

*Lactobacillus plantarum* strain RG14 (SEQ ID NO: 1)

| | |
|---|---|
| acgaactctg gtattgattg gtgcttgcat catgatttac atttgagtga gtggcgaact | 60 |
| ggtgagtaac acgtgggaaa cctgcccaga agcgggggat aacacctgga aacagatgct | 120 |
| aataccgcat aacaacttgg accgcatggt ccgagcttga aagatggctt cggctatcac | 180 |
| ttttggatgg tcccgcggcg tattagctag atggtggggt aacggctcac catggcaatg | 240 |
| atacgtagcc gacctgagag ggtaatcggc cacattggga ctgagacacg gcccaaactc | 300 |
| ctacgggagg cagcagtagg gaatcttcca caatggacga aagtctgatg gagcaacgcc | 360 |
| gcgtgagtga agaagggttt cggctcgtaa aactctgttg ttaaagaaga acatatctga | 420 |
| gagtaactgt tcaggtattg acggtattta accagaaagc cacggctaac tacgtgccag | 480 |
| cagccgcggt aatacgtagg tggcaagcgt tgtccggatt tattgggcgt aaagcgagcg | 540 |
| caggcggttt tttaagtctg at | 562 |

FIGURE 6: SEQUENCE LISTING OF *Lactobacillus plantarum*

*Lactobacillus plantarum* strain RI-11 (SEQ ID NO: 2)

| | |
|---|---|
| acgaactctg tattgattgg tgcttgcatc atgatttaca tttgagtgag tggcgaactg | 60 |
| gtgagtaaca cgtgggaaac ctgcccagaa gcggggggata cacctggaa acagatgcta | 120 |
| ataccgcata acaacttgga ccgcatggtc cgagcttgaa agatggcttc ggctatcact | 180 |
| tttggatggt cccgcggcgt attagctaga tggtggggta acggctcacc atggcaatga | 240 |
| tacgtagccg acctgagagg gtaatcggcc acattgggac tgagacacgg cccaaactcc | 300 |
| tacgggaggc agcagtaggg aatcttccac aatggacgaa agtctgatgg agcaacgccg | 360 |
| cgtgagtgaa gaagggtttc ggctcgtaaa actctgttgt taaagaagaa catatctgag | 420 |
| agtaactgtt caggtattga cggtatttaa ccagaaagcc acggctaact acgtgccagc | 480 |
| agccgcggta atacgtaggt ggcaagcgtt gtccggattt attgggcgta aagcgagcgc | 540 |
| aggcggtttt ttaagtctga t | 561 |

(FIGURE 6 continued)

*Lactobacillus plantarum* strain RS5 (SEQ ID NO: 3)

| | |
|---|---|
| acgaactctg gtattgattg gtgcttgcat catgatttac atttgagtga gtggcgaact | 60 |
| ggtgagtaac acgtgggaaa cctgcccaga agcgggggat aacacctgga aacagatgct | 120 |
| aataccgcat aacaacttgg accgcatggt ccgagcttga aagatggctt cggctatcac | 180 |
| ttttggatgg tcccgcggcg tattagctag atggtggggt aacggctcac catggcaatg | 240 |
| atacgtagcc gacctgagag ggtaatcggc cacattggga ctgagacacg gcccaaactc | 300 |
| ctacgggagg cagcagtagg gaatcttcca caatggacga aagtctgatg gagcaacgcc | 360 |
| gcgtgagtga agaagggttt cggctcgtaa aactctgttg ttaaagaaga acatatctga | 420 |
| gagtaactgt tcaggtattg acggtattta accagaaagc cacggctaac tacgtgccag | 480 |
| cagccgcggt aatacgtagg tggcaagcgt tgtccggatt tattgggcgt aaagcgagcg | 540 |
| caggcggttt tttaagtctg at | 562 |

(FIGURE 6 continued)

*Lactobacillus plantarum* strain RG11 (SEQ ID NO: 4)

| | |
|---|---|
| acgaactctg gtattgattg gtgcttgcat catgatttac atttgagtga gtggcgaact | 60 |
| ggtgagtaac acgtgggaaa cctgcccaga agcgggggat aacacctgga aacagatgct | 120 |
| aataccgcat aacaacttgg accgcatggt ccgagcttga aagatggctt cggctatcac | 180 |
| ttttggatgg tcccgcggcg tattagctag atggtggggt aacggctcac catggcaatg | 240 |
| atacgtagcc gacctgagag ggtaatcggc cacattggga ctgagacacg gcccaaactc | 300 |
| ctacgggagg cagcagtagg gaatcttcca caatggacga aagtctgatg gagcaacgcc | 360 |
| gcgtgagtga agaagggttt cggctcgtaa aactctgttg ttaaagaaga acatatctga | 420 |
| gagtaactgt tcaggtattg acggtattta accagaaagc cacggctaac tacgtgccag | 480 |
| cagccgcggt aatacgtagg tggcaagcgt tgtccggatt tattgggcgt aaagcgagcg | 540 |
| caggcggttt tttaagtctg at | 562 |

(FIGURE 6 continued)

*Lactobacillus plantarum* strain UL4 (SEQ ID NO: 5)

| | |
|---|---|
| acgaactctg gtattgattg gtgcttgcat catgatttac atttgagtga gtggcgaact | 60 |
| ggtgagtaac acgtgggaaa cctgcccaga agcgggggat aacacctgga aacagatgct | 120 |
| aataccgcat aacaacttgg accgcatggt ccgagcttga aagatggctt cggctatcac | 180 |
| ttttggatgg tcccgcggcg tattagctag atggtggggt aacggctcac catggcaatg | 240 |
| atacgtagcc gacctgagag ggtaatcggc cacattggga ctgagacacg gcccaaactc | 300 |
| ctacgggagg cagcagtagg gaatcttcca caatggacga aagtctgatg gagcaacgcc | 360 |
| gcgtgagtga agaagggttt cggctcgtaa aactctgttg ttaaagaaga acatatctga | 420 |
| gagtaactgt tcaggtattg acggtattta accagaaagc cacggctaac tacgtgccag | 480 |
| cagccgcggt aatacgtagg tggcaagcgt tgtcccggat ttattggccg taaagcgagc | 540 |
| gcaggcggtt ttttaagtct gat | 563 |

(FIGURE 6 continued)

*Lactobacillus plantarum* strain TL1 (SEQ ID NO: 6)

| | |
|---|---|
| acgaactctg gtattgattg gtgcttgcat catgatttac atttgagtga gtggcgaact | 60 |
| ggtgagtaac acgtgggaaa cctgcccaga agcgggggat aacacctgga aacagatgct | 120 |
| aataccgcat aacaacttgg accgcatggt ccgagcttga aagatggctt cggctatcac | 180 |
| ttttggatgg tcccgcggcg tattagctag atggtggggt aacggctcac catggcaatg | 240 |
| atacgtagcc gacctgagag ggtaatcggc cacattggga ctgagacacg gcccaaactc | 300 |
| ctacgggagg cagcagtagg gaatcttcca caatggacga aagtctgatg gagcaacgcc | 360 |
| gcgtgagtga agaagggttt cggctcgtaa aactctgttg ttaaagaaga acatatctga | 420 |
| gagtaactgt tcaggtattg acggtattta accagaaagc cacggctaac tacgtgccag | 480 |
| cagccgcggt aatacgtagg tggcaagcgt tgtccggatt tattgggcgt aaagcgagcg | 540 |
| caggcggttt tttaagtctg at | 562 |

TUMOUR CYTOTOXIC AGENT AND METHODS THEREOF

CROSS REFERENCE TO A RELATED APPLICATION

This application is a National Stage Application of International Application Number PCT/MY2010/000307, filed Nov. 29, 2010.

FIELD OF INVENTION

The present invention relates to a use of metabolites obtained from Gram-positive bacteria such as Lactic acid bacteria as an anti-tumour agent. Indeed, the present invention also discloses methods for treating and/or preventing tumour growth on human cells.

BACKGROUND OF INVENTION

Lactic acid bacteria that existed widely in the natural world are microbes of generating an organic acid by using a carbohydrate such as a glucose or lactose (von Wright, 2005). The Lactic acid bacterium has been directly or indirectly used in food from a long time ago. As a result of a research on an intestinal microflora of a man, it has been reported that the main Lactic acid bacteria in the gastrointestinal track of a healthy man are *Lactobacillus acidophilus, Lactobacillus casei, Lactobacillus fermentum, Lactobacillus plantarum* and so on. Such Lactic acid bacteria are resistant to gastric acid and bile (Balcazar, 2007). Presently, the Lactic acid bacterium has been widely used as a microbial agent or vital cell preparation of fermented goods and so on all over the world. There are many reports about the cytotoxic effect of fermented milk or Lactic acid bacteria on tumour cells. For example, the administration of *Lactobacillus casei* can prevent the development of colorectal cancer, with a daily intake of live *L. casei* suppressing atypia of colorectal tumours in 398 men and women who were free from tumours and who had at least two colorectal tumours removed (Ishikawa et al., 2005). Lactic acid bacteria are the bacteria metabolizing carbohydrate and producing lactic acid thereby. These bacteria belong to facultative anaerobes or obligatory anaerobes which proliferate well under anaerobic conditions. A few commonly known genuses of Lactic acid bacteria are *Streptococcus, Lactobacillus, Leuconostoc, Bifidobacteria* and *Pediococcus*. A *Streptococcus* genus microorganism is a homofermentative bacterium that generates lactic acid by fermenting milk to suppress putrefying bacteria or pathogenic bacteria. A *Lactobacillus* genus microorganism is a bacilliform, and a homo- or heterofermentative bacterium, which is widely seen in the fermentation of dairy products or vegetables. A *Leuconostoc* genus microorganism, a *diplococcus*, is a heterofermentative bacterium and mostly involved in fermenting vegetables. A *Bifidobacteria* genus microorganism is an obligatory anaerobe which generates L(+) lactic acid useful for children's health, but it cannot survive under aerobic conditions (Holzapfel et al., 2001).

Many chemical compositions have been reported as an anti-tumour agent. However, these compositions not only destroy the tumour cells, but also destroy normal cells. Alternatively, surgical treatment is generally performed to remove tumour tissue. However, this could be difficult as this method does not remove the tumour tissues thoroughly. It is said that the actual condition of any therapy provides side effects and does not fully acquire the best results. For example, chemotherapy has been successfully used as neoadjuvant, adjuvant and salvage strategies (Carlson et al., 2006). Chemotherapy targets rapidly dividing cancer cells, with deleterious side effect to rapidly dividing normal cells. This results in the most common side effects of chemotherapy such as endothelial toxicity, immunosuppression, mucositis and alopecia (Mitchell, 2004; Mailloux et al., 2005). Moreover, the use of conventional chemotherapeutic drugs has been proved to cause chemoresistance in cancer cells (Zhivotovsky and Orrenius, 2009). It is also used as concomitant treatment therapy with irradiation and biological agents (American Cancer Society, 2009). Despite much more advance in chemotherapy to surgery and irradiation, cancer mortality rate still ranks high among causes of mortality in many countries (WHO, 2009a). It is therefore essential to develop novel chemotherapeutics with greater efficacy while limited toxicity to normal cells.

The desire by consumers to use natural methods for health maintenance rather than long-term chemotherapeutics agents linked to their expectation that food becomes a source of prolonged well-being, supports the speculation that the probiotic market will expand rapidly. Results obtained from multidisciplinary research will probably essential for the positioning of probiotic preparations as either a food, a food supplement or as pharmaceutical preparation (Mercenier et al., 2002). Bacteriocins are isolated from Lactic acid bacteria and they exhibit inhibitory effects against various pathogens in a manner similar to antibiotics. However, bacteriocins are distinguishable from antibiotics in terms of their synthesis, mode of action, toxicity and resistance mechanisms.

New antitumour compound are continually in demand, for the treatment of cancer in man and the production of new anticancer compounds is an important feature of developing antitumour agents for further studies. Equally important are novel strains of cultures used in the production processes for preparing these compounds. Additionally, it has been determined that the metabolites produced by certain microorganism exhibited antimicrobial activity against important human pathogenic bacteria and fungi, as well as having antiviral and anti-tumour activities (Zhao et al., 2006; Wachsman et al., 1999).

An object of the present invention is to provide a novel antitumour agent which has excellent antitumour activity based on metabolites with reduced side effects and which can be prepared starting with a highly safe bacterium used in food production. Yet, another objective of this present invention provides methods of measuring anticancer efficacy (cancer-cell-growth inhibition and apoptosis induction) of Lactic acid bacteria, and further to provide screening method of the Lactic acid bacteria which have anticancer efficacy.

SUMMARY OF INVENTION

Accordingly, the present invention relates to the use of a Lactic acid bacteria strains to prevent or treat a tumour, wherein the bacteria strains being *Lactobacillus plantarum* I-UL4 having accession number NRRL B67067, TL1 having accession number NRRL B67068, RS5 having accession number NRRL B67069, RG14 having accession number NRRL B67071, RG11 having accession number NRRL B67070 and RI11 having accession number NRRL B67072 deposited at the Agricultureal Research Culture Collection (NRRL) in Peoria, Ill., USA, an international Deposit Authorities recognized under the Budapest Treaty (the bacteria strains are in a live form or none live but intact). Moreover, the *Lactobacillus plantarum* I-UL4 (NRRL B67067), TL1 (NRRL B67068), RS5 (NRRL B67069), RG14 (NRRL B67071), RG11 (NRRL B67070) and RI11 (NRRL B67072) is said to produce metabolite(s) such as bacteriocins which is capable to inhibit proliferation and induce apoptosis of cancer in a mammal (preferably human being) in order to prevent or treat tumour. In particular, the metabolite is an anti-tumour agent and the metabolite(s) is supported with nutrients, vitamin (preferably vitamin B), salt of organic acids (preferably sodium salt of formic acid, acetic acid and lactic acid)r combination thereof. Indeed, the amount of metabolite(s) use in this particular invention is at a range between 0% (v/v) and 50% (v/v) of the total complete growth media. Following to this, it is said that the anti-tumour agent provides the means of reducing viability in various types of human cancerous cells (e.g human breast cancer cell line MCF-7, human colorectal cancer cell line HT-29, human cervical cancer cell line HeLa, human liver cancer cell line Hep G2, human leukemia cell lines HL-60 and K-562) by providing a concentration of 1% (v/v) to 50% (v/v). In addition, the anti-tumour agent provides the means of inhibiting the proliferation in various types of human cancerous cells by having a concentration of 1% (v/v) to 50% (v/v). Also, the present invention illustrate Lactic acid bacteria strains having to facilitate induction of apoptosis of the cells of a cancer, wherein the strains being *Lactobacillus plantarum* I-UL4 (NRRL B67067), TL1 (NRRL B67068), RS5 (NRRL B67069), RG14 (NRRL B67071), RG11 (NRRL B67070) and RI11 (NRRL B67072) deposited at the NRRL. Accordingly, the present invention discloses manufacturing of a drug destined for the treatment or prevention of cancer, wherein the drug is manufactured by means of *Lactobacillus plantarum* I-UL4 (NRRL B67067), TL1 (NRRL B67068), RS5 (NRRL B67069), RG14 (NRRL B67071), RG11 (NRRL B67070) and RI11 (NRRL B67072) strains. In fact, the anti-tumour agent also provides a combination of 6 types of metabolites derived from *Lactobacillus plantarum* I-UL4 (NRRL B67067), TL1 (NRRL B67068), RS5 (NRRL B67069), RG14 (NRRL B67071), RG11 (NRRL B67070) and RI11 (NRRL B67072) deposited at the NRRL.

Yet, another aspect of the present invention relates to composition to treat or prevent cancer, comprising an effective quantity of at least one Lactic acid bacteria strains and a pharmaceutically acceptable vehicle, said strain(s) being *Lactobacillus plantarum* I-UL4 (NRRL B67067), TL1 (NRRL B67068), RS5 (NRRL B67069), RG14(NRRL B67071), RG11 (NRRL B67070) and RI11 (NRRL B67072) is deposited at the NRRL. It is said that, the composition contains an anti-tumour agent which include metabolites such as bacteriocins and organic acids (includes sodium salt of formic acid, acetic acid and lactic acid) and further contains nutrients, vitamin(preferably vitamin B), and salt of organic acids or combination thereof. Also, the composition further includes a combination of 6 metabolites derived from *Lactobacillus plantarum* I-UL4 (NRRL B67067), TL1 (NRRL B67068), RS5 (NRRL B67069), RG14 (NRRL B67071), RG11 (NRRL B67070) and RI11 (NRRL B67072) strains deposited at the NRRL.

In addition, the present invention also relates to a method to facilitate apoptosis of cancer cells in a mammal (human being) and the method comprises the administration the composition mentioned above. In particular, this invention preferably provides a kit for preventing or treating a cancer in a mammal, wherein the kit comprises a container containing the composition as mentioned above. Also, the present invention discloses foodstuffs for anti-tumour containing *Lactobacillus plantarum* I-UL4 (NRRL B67067), TL1 (NRRL B67068), RS5 (NRRL B67069), RG14 (NRRL B67071), RG11 (NRRL B67070) and RI11 (NRRL B67072) strains deposited at the NRRL. Also, the foodstuffs includes a combination of 6 metabolites derived from *Lactobacillus plantarum* I-UL4 (NRRL B67067), TL1 (NRRL B67068), RS5 (NRRL B67069), RG14 (NRRL B67071), RG11 (NRRL B67070)and RI11 (NRRL B67072) strains.

BRIEF DESCRIPTION OF THE SEQUENCES

SEQ ID NO:1 is a nucleotide sequence for *Lactobacillus plantarum* strain RG14 in accordance with the subject invention.

SEQ ID NO:2 is a nucleotide sequence for *Lactobacillus plantarum* strain RI11 in accordance with the subject invention.

SEQ ID NO:3 is a nucleotide sequence for *Lactobacillus plantarum* strain RS5 in accordance with the subject invention.

SEQ ID NO:4 is a nucleotide sequence for *Lactobacillus plantarum* strain RG11 in accordance with the subject invention.

SEQ ID NO:5 is a nucleotide sequence for *Lactobacillus plantarum* strain UL4 in accordance with the subject invention.

SEQ ID NO:6 is a nucleotide sequence for *Lactobacillus plantarum* strain TL1 in accordance with the subject invention.

BRIEF DESCRIPTION OF THE DRAWINGS

The present invention will be fully understood from the detailed description given herein below and the accompanying drawings which are given by way of illustration only, and thus are not limitative of the present invention, wherein:

FIG. 1 is a graph of anti-proliferative effect of metabolites derived from the six strains of Lactic acid bacteria on MCF-7 cells. Values within the same row and experiment having an asterisk are significantly different from untreated control, $P<0.05$.

FIG. 2 is a graph of anti-proliferative effect of metabolites derived from the six strains of Lactic acid bacteria on HT-29 cells. Values within the same row and experiment having an asterisk are significantly different from untreated control, $P<0.05$.

FIG. 3 is a graph of apoptosis induction of Lactic acid bacteria metabolites on MCF-7 cells. Notes: "early apop" indicated early apoptotic cells and "late apop" indicated late apoptotic cells and necrotic cells. T1: untreated control; T2: treatment group (±indicates standard error). The treatment group is compared to untreated control. Values within the same row and experiment sharing a common superscript letter are not significantly different, $P>0.05$.

FIG. 4 is a picture of fluorescence photomicrographs of MCF-7 cells treated with UL4 (NRRL B67067) metabolite. Panel A: 24 hours, B: 48 hours and C: 72 hours. Morphological changes following exposure to Lactic acid bacteria metabolite are typical of apoptosis, showing ↑a=cell shrinkage, ↑b=membrane blebbing, ↑c=apoptotic bodies formation, and ↑d, necrotic cells. (Magnification: 400×).

FIG. 5 is a graph of two-parameter scatterplots (left panel) and single parameter histogram (right panel) illustrating the detection of DNA strand breaks in apoptotic cells by TUNEL assay. Panel A: 72h untreated control; B: 72h treated with UL4 (NRRL B67067) metabolite. Apoptotic cells (R4) are characterized by very high frequency of DNA strand breaks (note exponential scale of Y coordinate) in scatterplots and M2 gate in histogram.

FIG. 6 is a sequence listing of *Lactobacillus plantarum* I-UL4 (NRRL B67067) (SEQ ID NO:5), TL1 (NRRL B67068) (SEQ ID NO:6), RS5 (NRRL B67069) (SEQ ID NO:3), RG14 (NRRL B67071) (SEQ ID NO:1), RG11 (NRRL B67070) (SEQ ID NO:4) and RI11 (NRRL B67072) (SEQ ID NO:2) strains deposited at the NRRL.

DETAILED DESCRIPTION OF THE INVENTION

In particular, the present invention describes the cytotoxic effects of metabolites of Lactic acid bacteria strains isolated from Malaysian foods, *Lactobacillus* sp., on various cancerous cells without cytotoxic effects on normal cells. The present invention also relates to the induction of cell death on human cancerous cells. More particularly, the present invention relates to inhibition of proliferation of colon and breast cancer cells. More specifically, the present invention relates to the induction of apoptosis on human breast cancer cells.

It was demonstrated that the present invention provides a method for easily measuring the antitumour effect of Lactic acid bacterium, a method for screening a Lactic acid bacterium having an antitumour effect by using the method, a method for easily measuring an anti-inflammatory cytokine effect of Lactic acid bacterium and a method for screening a Lactic acid bacterium having an inflammatory cytokine inhibitory effect by using the method.

The solution is based on that the present invention, relates to a novel *Lactobacillus* genus microorganism and more particularly, *Lactobacillus plantarum* including I-UL4 (NRRL B67067), TL1 (NRRL B67068), RS5 (NRRL B67069), RG14 (NRRL B67071), RG11 (NRRL B67070) and RI11 (NRRL B67072) strains isolated from food sources.

A culture of each microbe has been deposited with the Agricultural Research Service Collection NRRL International Depository Authority, 1815 N. University Street, Peoria Ill., 616104, USA. As shown in the table below, the deposits have been assigned accession numbers NRRL B67067, NRRL B67068, NRRL B67069, NRRL B67071, NRRL B67070, and NRRL B67072 by the repository.

| Strain | Deposit Number | Deposit Date |
|---|---|---|
| I-UL4 | NRRL B67067 | Jun. 17, 2015 |
| TL1 | NRRL B67068 | Jun. 17, 2015 |
| RS5 | NRRL B67069 | Jun. 17, 2015 |
| RG14 | NRRL B67071 | Jun. 17, 2015 |
| RG11 | NRRL B67070 | Jun. 17, 2015 |
| RI11 | NRRL B67072 | Jun. 17, 2015 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

In particular, these strains are said to be having immune enhancement, anticancer activities and a use thereof. Due to its excellent anticancer activities by reducing the cancer cell viability, inhibition on proliferation of cancer cells and induction of apoptosis on human cancer cells, the *Lactobacillus plantarum* including I-UL4 (NRRL B67067), TL1 (NRRL B67068), RS5 (NRRL B67069), RG14 (NRRL B67071), RG11 (NRRL B67070) and RI11 (NRRL B67072) strains of the present invention can be effectively used for the production of various products such as anticancer agent, food additive, feed additive, health supplement or functional food in nutraceutical industry and pharmaceutical products.

Accordingly, the I-UL4 (NRRL B67067), TL1 (NRRL B67068), RS5 (NRRL B67069), RG14 (NRRL B67071), RG11 (NRRL B67070) and RI11 (NRRL B67072) strains were obtained from the Department of Bioprocess Technology, University Putra Malaysia.

Without being limited to theory, it is believed that the metabolites derived from probiotic Lactic acid bacteria are capable of significantly reducing cancer cell viability, inhibiting proliferation of cancer cells and inducing apoptosis on human cancer cells. See working examples herein for further details.

BEST MODE TO CARRY OUT THE INVENTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. When a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. When the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. It must be noted that as used herein and in the appended claims, the singular forms "a," "an," and "the" include plural referents unless the context clearly dictates otherwise.

EXAMPLES

The following example serves to illustrate the scope of the use of the present invention and not to limit its scope. Modifications and variations may be made to it without going away from neither the spirit nor the scope of the invention. Even though one may use other methods or products equivalent to those that we find hereinafter to test or to carry out the present invention, the material and the preferred methods are described. In the context of the present invention, in order to determine how the Lactic acid bacteria help in the apoptosis of cancer, trials have been conducted on the human breast cancer cell line MCF-7, human colorectal cancer cell line HT-29, human cervical cancer cell line HeLa, human liver cancer cell line Hep G2, human leukemia cell lines HL-60 and K-562. The Lactic acid bacteria used constitute of *Lactobacillus plantarum* including I-UL4 (NRRL B67067), TL1 (NRRL B67068), RS5 (NRRL B67069), RG14 (NRRL B67071), RG11 (NRRL B67070) and RI11 (NRRL B67072) strains. Additionally, these strains produce metabolite/s which acts as an anti-tumour agent or cytotoxic agent. Yet, in this present invention, the anti-tumour agent or cytotoxic agent is supported by bacteriocins, nutrients, vitamin, salt of organic acids.

Preparing Metabolite i) The metabolites of *Lactobacillus* sp. was transferred to fresh universal bottle and the pH of the metabolites was adjusted to physiological pH (between 7.2 and 7.4) using NaOH. The metabolites was filtered through 0.22 μm membrane syringe filter (Milipore, USA) prior to treatment on both cancerous cell lines and normal cells.

Obtaining Cell Line i) The Animal Tissue Culture Laboratory of Universiti Putra Malaysia provided the human breast cancer cell line MCF-7, human colorectal cancer cell line HT-29, human cervical cancer cell line HeLa, human liver cancer cell line Hep G2, human leukemia cell lines HL-60 and K-562. As for non-malignant normal glandular epithelium cells MCF-10A which was used as a model of normal glandular epithelium was obtained from the American Type Culture Collection (ATCC). All cancer and normal cell lines were maintained in the ATCC recommended medium supplemented with 10% (v/v) heat-inactivated Foetal Bovine Serum and 100 U/ml penicillin-streptomycin, and incubated at 37° C. in 5% $CO_2$ atmosphere.

ii) All animal experiments were conducted adhering to the guidelines of Faculty of Veterinary and Animal Sciences, Universiti Putra Malaysia. The 7-8 weeks old male ICR mice were sacrificed by cervical dislocation. The spleen and thymus obtained after dissection were rinsed 2-3 times with ice-cold PBS followed by mincing on a wire mesh soaked in PBS. The cell suspension was filtered using a wire mesh to remove any cell clumps. All the cells obtained were washed 2-3 times with ice-cold PBS by centrifugation (300×g for 5 min).

(ii) With the guideline and consent obtained from Faculty of Veterinary and Animal Sciences, Universiti Putra Malaysia, about 10 ml of blood was drawn (venipuncture) aseptically from healthy human volunteers (25-30 years of age) and transferred to preservative free heparin tube. Anticoagulated blood was diluted with equal volume of pH 7.5 phosphate buffered saline (PBS) and slowly layered over Ficoll-Paque Plus. The mixture was centrifuged in a swinging bucket rotor at 400×g for 40 min at 18-20° C. Peripheral blood mononuclear cells (PBMC) were collected from Ficoll-plasma interface and washed twice with PBS. The cells pellets of mice splenocytes, thymocytes and human PBMC were resuspended in complete growth media with density of $5\times10^5$ cells/ml.

Measures of Viability of Cancer Cells, Proliferation and Apoptosis Induction i) The effect of metabolites derived from six strains of locally isolated *Lactobacillus* sp. on cell viability was assessed using MTT assay according to Mosmann (1983). Cells were plated onto flat-bottomed 96-well plates at the density of $1\times10^4$ cells/well for 24 h prior to treatment [control cells, 0% (v/v) of metabolites] or in the presence of two-fold dilution of concentrations [50% (v/v) to 0.5% (v/v)] of metabolites. After 24 h, 48 h, and 72 h of incubation respectively, 20 μl of MIT solution (5 mg/ml in PBS) was added to each well and incubated in the dark for 4 h at 37° C. and 5% $CO_2$ atmospheric condition. The resultant formazan crystals were dissolved in 100 μl of DMSO. The absorbance (A) at 570 nm with reference wavelength of 630 nm was then recorded using μ Quant ELIZA reader (Biotek EL340, USA). Percentage of cell viability is calculated as $(A_{sample}-A_{blank})/(A_{control}-A_{blank})\times 100\%$. All experiments were conducted in three independent experiments with triplicate samples for each experiment and the concentration of 50% inhibition ($IC_{50}$) values were determined.

TABLE 1

Concentration of metabolites derived from six strains of *Lactobacillus* sp. showing 50% inhibition ($IC_{50}$ values) on various cancer cell lines and normal cells after 72 h of incubation.

| Type of cells | $IC_{50}$ values of metabolites derived from *Lactobacillus* sp. | | | | | |
|---|---|---|---|---|---|---|
| | UL4 | TL1 | RS5 | RG14 | RG11 | RI11 |
| Cancer cell lines | | | | | | |
| MCF-7 cells | 10 | 13 | 21 | 20 | 16 | 16 |
| HeLa | 20 | 18 | 24 | 20 | N.D. | 18 |
| Hep G2 | 22 | 22 | 27 | 22 | N.D. | N.D. |
| HT-29 | N.D. | N.D. | 28 | 22 | N.D. | N.D. |
| K-562 | 10 | 5 | 5 | 5 | 5 | 5 |
| HL-60 | 5 | 5 | 9 | 10 | 1 | 1 |
| Normal cells | | | | | | |
| MCF-10A | 26 | N.D. | N.D. | N.D. | N.D. | N.D. |
| Human PBMC | N.D. | N.D. | N.D. | N.D. | N.D. | N.D. |
| Mice splenocytes | N.D. | N.D. | N.D. | N.D. | N.D. | N.D. |
| Mice thymocytes | N.D. | N.D. | N.D. | N.D. | N.D. | N.D. |

Notes:
$IC_{50}$ value, % (v/v) of metabolites causing 50% inhibition of cell viability of treated cells.
N.D., no $IC_{50}$ value was detected up to concentration of 50% (v/v).

iii) Cells were seeded at $5\times10^3$ cells/well in 96-well plate. The medium was aspirated after 24 h and replaced with fresh medium containing the test extract to be studied for 24 h, 48 h and 72 h, respectively. Further procedure was carried out according to protocol from manufacturer. Using a BrdU ELISA system as an alternative to the radioactive [$^3$H] thymidine incorporation assay, cells were reincubated with BrdU subsequently to a final concentration of 10 μM for 2-24 h. Medium was aspirated from each well. Fixative/denaturing solution was added to enable antibody binding to the incorporated BrdU where cells were fixed, permeabilized and the DNA denatured. Anti-BrdU antibody was added to every well and incubated for 1 h to bind to incorporated BrdU. Unbound antibody was then washed away and horseradish peroxidase-conjugated goat anti-mouse which binds to the detector antibody was added. Stop solution was added to each well before the colored reaction product is quantified by measuring the absorbance of each well at 450 nm (reference wavelength 540 nm) using spectrophotometer (Biotek EL340, USA).

iv) One of the hallmarks of apoptotic cells is the externalization of phosphatidylserine (PS). In principle, annexin V detects cell surface phosphatidylserine while PI stains cellular DNA of cells with compromised cell membranes. This allows the discrimination of viable cells (annexin $V^-/PI^-$) from early apoptotic cells (annexin $V^+/PI^-$) and late apoptotic and necrotic cells (annexin $V^+/PI^+$). In this study, mode of cell death was examined using the BD Biosciences Annexin V-FITC Apoptosis Detection Kit. MCF-7 cells were seeded into six-well tissue culture plates at a density of $2.5 \times 10^5$ cells/well and allowed to attach overnight, followed by treatment for 24, 48 and 72 h. At the end of treatment, detached and trypsinised cells were pelleted down and resuspended in binding buffer. Cells were then stained with annexin V-FITC and PI for 15 min in the dark and diluted with binding buffer to a final volume of 500 µl before flow cytometry analysis. A total of 10,000 events per sample were acquired (Vermes et al., 1995). Data acquisition and analysis were performed on FACS-Calibur flow cytometer (BD Biosciences, USA). Results are expressed as the mean±SEM of at least three separate experiments.

v) MCF-7 cells were treated with UL4 (NRRL B67067) metabolite in six well plates and were incubated in 5% $CO_2$ atmospheric condition at 37° C. for 24, 48 and 72 hours. After 24, 48 and hours of incubation, respectively, detached cells in the medium were collected and added back to trypsinised adherent cells. The cells were washed with PBS and then incubated with 10 µl of AO (100 µg/mL) and PI (100 µg/mL) at a ratio of 1:1 in 1 mL of cells and recentrifuged at 200×g for 5 min. The supernatant was aspirated, leaving 50 µl of remnant supernatant. The pellet was resuspended and 10 µl of cell suspension was dripped on slide and covered with cover slip. Within 30 min, the slide was observed under fluorescent microscope (Nikon FC-35DX, Japan) with combination of excitation filter and barrier filter of 450-490 nm and long pass filter of 520 nm. The percentages of viable (green intact cells), apoptotic (green shrinking cells with condensed or fragmented nucleus), and late apoptotic and necrotic (red cells) were determined from >200 cells for the data to be statistically significant.

vi) Cells treated with UL4 (NRRL B67067) metabolite were harvested after incubation period of 24, 48 and 72 hours. The detached and trypsinised cells were pelleted and fixed with ice cold 80% ethanol drop by drop and incubate at 4° C. until analysis (minimum 2 hours). Then, the cell was pelleted again and washed with PBS-BSA-Az-EDTA buffer for twice. The cells were pulse-vortexed to elute the DNA fragments. For DNA analysis, cells were stained in PBS buffer consists of 0.1% (v/v) Triton X-100, 10 mM EDTA, 50 µg/mL RNase A and 2 µg/mL PI. This process was carried out in the dark because PI is sensitive to light. The cell was then incubated for 30 min at 4° C. and then read with FACS-Calibur flow cytometer (BD Biosciences, USA) at Animal Tissue Culture Laboratory, Department of Molecular Biology, Faculty of Biotechnology and Biomolecular Sciences, University Putra Malaysia within 24 hours. Ten thousand events per samples were acquired. Doublets and cell debris were gated off in DNA dot plot view before calculation. Cell cycle distribution was calculated using CELLQuest Pro software (BD Biosciences, USA). The experiment was repeated for at least three times with triplicated samples for each experiment.

TABLE 2

Effect of UL4 metabolite on cell cycle phases distribution of MCF-7

|  | untreated control (%) | UL4 metabolite (%) |
|---|---|---|
| 24 hours | | |
| Sub- $G_0/G_1$ | 0.5 ± 0.3 | 1.7 ± 1.6 |
| $G_0/G_1$ | 59.1 ± 3.1 | 64.5 ± 6.7 |
| S | 21.4 ± 4.2 | 16.4 ± 3.6 |
| M | 19.3 ± 1.6 | 17.6 ± 3.3 |
| 48 hours | | |
| Sub- $G_0/G_1$ | 0.5 ± 0.2 | 14.3* ± 5.6 |
| $G_0/G_1$ | 80.1 ± 6.2 | 62.7 ± 2.1 |
| S | 9.4 ± 3.7 | 13.7 ± 2.7 |
| M | 10.1 ± 2.6 | 9.7 ± 1.1 |
| 72 hours | | |
| Sub- $G_0/G_1$ | 0.5 ± 0.1 | 9.5* ± 4.7 |
| $G_0/G_1$ | 89.9 ± 1.4 | 70.2 ± 3.4 |
| S | 3.3 ± 0.4 | 9.9 ± 1.1 |
| M | 6.2 ± 1.5 | 10.1 ± 1.2 |

Notes:
The data shown above the bars represent the mean of percentage of cells. Error bars represent SEM. Values within the same row and experiment having an asterick are significantly different (P > 0.05).

(vi) DNA labeling was carried out using BD Biosciences APO-DIRECT Kit. Cells were seeded at $2 \times 10^5$ cells/well in six-well tissue culture plate. After 24 hours, the medium was replaced with fresh medium containing the test extracts to be studied at the desired concentrations. Further procedure was done according to manufacturer's instructions. After incubation, the detached and trypsinised cells were pelleted and resuspended in 1% (w/v) paraformaldehyde in PBS (pH 7.4) at a concentration of $1-2 \times 10^6$ cells/mL. The cell suspension was placed on ice for 30-60 min. Fixed cells were then collected by centrifugation at 300×g for 5 min and the supernatant was discarded. The cell pellets were washed twice in 5 mL of PBS and were resuspended in the residual PBS in tubes by gently vortexing. Subsequently, cells were resuspended in 70% (v/v) ice-cold ethanol and left for a minimum of 30 min on ice before being stored at −20° C. After appropriate storage time (1-7 days), the cell suspension was centrifuged at 300×g for 5 min and the 70% v/v ethanol was aspirated. The cells were washed with 1 mL of Wash Buffer twice and the cell pellet was resuspended in 50 µl of the DNA Labeling Solution.

After incubation of 60 min, the cells were rinsed with 1 mL of Rinse Buffer twice and pelleted by centrifugation at 300×g for 5 min. The cell pellet was stained with 0.5 mL of the PI/RNase Staining Buffer. The cells were incubated in dark for 30 min at RT and analyzed by FACS-Calibur flow cytometry using CELLQuest Pro software within 3 hours. Ten thousand events per sample were acquired with the cell doublets and debris were gated off in DNA dot plot view before calculation.

Results were expressed as mean±S.E and analyzed by General Linear Model. The statistical analysis was conducted using Minitab Statistical Software at differences of P<0.05.

The invention claimed is:

1. A method for treating a tumour wherein said method comprises administering, to a subject in need of such treatment, an anti-tumour agent that comprises a bacteria strain, and/or a metabolite from said bacteria strain, wherein said bacteria strain is selected from the group consisting of *Lactobacillus plantarum* I-UL4(NRRL B67067), TL1 (NRRL B67068), RS5 (NRRL B67069), RG14 (NRRL B67071), RG11 (NRRL B67070) and RI11 (NRRL B67072) deposited at the Agricultural Research Culture Collection (NRRL), an International Deposit Authority recognized under the Budapest Treaty.

2. The method according to claim 1, wherein the bacteria strain is in a live form or a non-live, but intact, form.

3. The method according to claim 1, wherein the bacteria strain produces a metabolite that inhibits proliferation and induces apoptosis of cancer in a mammal.

4. The method according to claim 3, wherein the mammal is a human.

5. The method according to claim 3, wherein the metabolite is a bacteriocin.

6. The method according to claim 1, wherein the metabolite is supported with a nutrient, vitamin, salt of an organic acid, or a combination thereof.

7. The method according to claim 6, wherein the vitamin is vitamin B.

8. The method according to claim 6, wherein the salt of an organic acid is the sodium salt of formic acid, acetic acid or lactic acid.

9. The method according to claim 1, wherein the bacteria strain is grown in a total complete growth medium and the metabolite is present at between 0% (v/v) and 50% (v/v) of the medium.

10. The method according to claim 1, wherein the metabolite can reduce viability in human cancerous cells when present at a concentration of 1% (v/v) to 50% (v/v).

11. The method according to claim 10, wherein the human cancerous cells are human breast cancer cell line MCF-7, human colorectal cancer cell line HT-29, human cervical cancer cell line HeLa, human liver cancer cell line Hep G2, human leukemia cell lines HL-60 or K-562.

12. The method according to claim 1, wherein the metabolite can inhibit the proliferation of human cancerous cells when present at a concentration of 1% (v/v) to 50% (v/v).

13. The method according to claim 10, wherein the human cancerous cells are human breast cancer cell line MCF-7 or human colorectal cancer cell line HT-29.

14. A method for inducing apoptosis of cancer cells, wherein the method comprises administering to the cancer cells a lactic acid bacteria strain, or a metabolite produced by said strain, wherein said strain is selected from the group consisting of *Lactobacillus plantarum* I-UL4 (NRRL B67067), TL1 (NRRL B67068), RS5 (NRRL B67069), RG14 (NRRL B67071), RG11(NRRL B67070) and RI11 (NRRL B67072) deposited at the NRRL, an International Deposit Authority recognized under the Budapest Treaty.

15. The method according to claim 1, wherein the anti-tumour agent comprises a combination of metabolites derived from *Lactobacillus plantarum* I-UL4 (NRRL B67067), TL1(NRRL B67068), RS5 (NRRL B67069), RG14 (NRRL B67071), RG11 (NRRL B67070) and RI11 (NRRL, B67072).

16. A method to facilitate apoptosis of cancer cells in a mammal, wherein the method comprises administering to the mammal an effective quantity of at least one lactic acid bacteria strain, and/or a metabolite from said bacteria strain, and a pharmaceutically acceptable vehicle, wherein said bacteria strain is selected from the group consisting of *Lactobacillus plantarum* I-UL4 (NRRL B67067), TL1 (NRRL B67068), RS5 (NRRL B67069), RG14 (NRRL 867071), RG11 (NRRL B67070) and RI11 (NRRL B67072) deposited at NRRL.

17. The method according to claim 16, wherein the mammal is a human.

18. (The method according to claim 1, wherein the said bacteria strain is *Lactobacillus plantarum* I-UL4 (NRRL B67067).

19. The method according to claim 1, wherein the said bacteria strain is *Lactobacillus plantarum* TL1 (NRRL B67068).

20. The method according to claim 1, wherein the said bacteria strain is *Lactobacillus plantarum* RS5 (NRRL B67069).

21. The method according to claim 1, wherein the said bacteria strain is *Lactobacillus plantarum* RG14 (NRRL B67071).

22. The method according to claim 1, wherein the said bacteria strain is *Lactobacillus plantarum* RG11 (NRRL B67070).

23. The method according to claim 1, wherein the said bacteria strain is *Lactobacillus plantarum* RI11 (NRRL B67072).

* * * * *

SEQUENCE LISTING

<160> NUMBER OF SEQ ID NOS: 6

<210> SEQ ID NO 1
<211> LENGTH: 562
<212> TYPE: DNA
<213> ORGANISM: Lactobacillus plantarum
<220> FEATURE:
<221> NAME/KEY: misc_feature
<223> OTHER INFORMATION: Lactobacillus plantarum strain RG14

<400> SEQUENCE: 1

```
acgaactctg gtattgattg gtgcttgcat catgatttac atttgagtga gtggcgaact      60
ggtgagtaac acgtgggaaa cctgcccaga agcgggggat aacacctgga aacagatgct    120
aataccgcat aacaacttgg accgcatggt ccgagcttga agatggctt cggctatcac     180
ttttggatgg tcccgcggcg tattagctag atggtggggt aacggctcac catggcaatg   240
atacgtagcc gacctgagag ggtaatcggc cacattggga ctgagacacg gcccaaactc   300
ctacgggagg cagcagtagg gaatcttcca caatggacga aagtctgatg gagcaacgcc    360
gcgtgagtga agaagggttt cggctcgtaa aactctgttg ttaaagaaga acatatctga   420
gagtaactgt tcaggtattg acggtattta accagaaagc cacggctaac tacgtgccag   480
cagccgcggt aatacgtagg tggcaagcgt tgtccggatt tattgggcgt aaagcgagcg   540
caggcggttt tttaagtctg at                                             562
```

<210> SEQ ID NO 2
<211> LENGTH: 561
<212> TYPE: DNA
<213> ORGANISM: Lactobacillus plantarum
<220> FEATURE:
<221> NAME/KEY: misc_feature
<223> OTHER INFORMATION: Lactobacillus plantarum strain RI-11

<400> SEQUENCE: 2

```
acgaactctg tattgattgg tgcttgcatc atgatttaca tttgagtgag tggcgaactg      60
gtgagtaaca cgtgggaaac ctgcccagaa gcggggata acacctggaa acagatgcta    120
ataccgcata acaacttgga ccgcatggtc cgagcttgaa agatggcttc ggctatcact   180
tttggatggt cccgcggcgt attagctaga tggtggggta acggctcacc atggcaatga   240
tacgtagccg acctgagagg gtaatcggcc acattgggac tgagacacgg cccaaactcc   300
tacgggaggc agcagtaggg aatcttccac aatggacgaa agtctgatgg agcaacgccg   360
cgtgagtgaa gaagggtttc ggctcgtaaa actctgttgt taaagaagaa catatctgag   420
agtaactgtt caggtattga cggtatttaa ccagaaagcc acggctaact acgtgccagc   480
agccgcggta atacgtaggt ggcaagcgtt gtccggattt attgggcgta aagcgagcgc   540
aggcggtttt ttaagtctga t                                              561
```

<210> SEQ ID NO 3
<211> LENGTH: 562
<212> TYPE: DNA
<213> ORGANISM: Lactobacillus plantarum
<220> FEATURE:
<221> NAME/KEY: misc_feature
<223> OTHER INFORMATION: Lactobacillus plantarum strain RS5

<400> SEQUENCE: 3

```
acgaactctg gtattgattg gtgcttgcat catgatttac atttgagtga gtggcgaact      60
ggtgagtaac acgtgggaaa cctgcccaga agcgggggat aacacctgga aacagatgct    120
```

```
aataccgcat aacaacttgg accgcatggt ccgagtttga agatggcttt cggctatcac      180
ttttggatgg tcccgcggcg tattagctag atggtggggt aacggctcac catggcaatg      240
atacgtagcc gacctgagag ggtaatcggc cacattggga ctgagacacg gcccaaactc      300
ctacgggagg cagcagtagg gaatcttcca caatggacga aagtctgatg gagcaacgcc      360
gcgtgagtga agaagggttt cggctcgtaa aactctgttg ttaaagaaga acatatctga      420
gagtaactgt tcaggtattg acggtattta accagaaagc cacggctaac tacgtgccag      480
cagccgcggt aatacgtagg tggcaagcgt tgtccggatt tattgggcgt aaagcgagcg      540
caggcggttt tttaagtctg at                                               562

<210> SEQ ID NO 4
<211> LENGTH: 562
<212> TYPE: DNA
<213> ORGANISM: Lactobacillus plantarum
<220> FEATURE:
<221> NAME/KEY: misc_feature
<223> OTHER INFORMATION: Lactobacillus plantarum strain RG11

<400> SEQUENCE: 4
acgaactctg gtattgattg gtgcttgcat catgatttac atttgagtga gtggcgaact       60
ggtgagtaac acgtgggaaa cctgcccaga agcgggggat aacacctgga aacagatgct      120
aataccgcat aacaacttgg accgcatggt ccgagtttga agatggcttt cggctatcac      180
ttttggatgg tcccgcggcg tattagctag atggtggggt aacggctcac catggcaatg      240
atacgtagcc gacctgagag ggtaatcggc cacattggga ctgagacacg gcccaaactc      300
ctacgggagg cagcagtagg gaatcttcca caatggacga aagtctgatg gagcaacgcc      360
gcgtgagtga agaagggttt cggctcgtaa aactctgttg ttaaagaaga acatatctga      420
gagtaactgt tcaggtattg acggtattta accagaaagc cacggctaac tacgtgccag      480
cagccgcggt aatacgtagg tggcaagcgt tgtccggatt tattgggcgt aaagcgagcg      540
caggcggttt tttaagtctg at                                               562

<210> SEQ ID NO 5
<211> LENGTH: 563
<212> TYPE: DNA
<213> ORGANISM: Lactobacillus plantarum
<220> FEATURE:
<221> NAME/KEY: misc_feature
<223> OTHER INFORMATION: Lactobacillus plantarum strain UL4

<400> SEQUENCE: 5
acgaactctg gtattgattg gtgcttgcat catgatttac atttgagtga gtggcgaact       60
ggtgagtaac acgtgggaaa cctgcccaga agcgggggat aacacctgga aacagatgct      120
aataccgcat aacaacttgg accgcatggt ccgagcttga agatggcttt cggctatcac      180
ttttggatgg tcccgcggcg tattagctag atggtggggt aacggctcac catggcaatg      240
atacgtagcc gacctgagag ggtaatcggc cacattggga ctgagacacg gcccaaactc      300
ctacgggagg cagcagtagg gaatcttcca caatgggacg aaagtctgat ggagcaacgc      360
cgcgtgagtg aagaaggttt cggctcgtaa aactctgttg ttaaagaaga acatatctga      420
gagtaactgt tcaggtattg acggtattta accagaaagc cacggctaac tacgtgccag      480
cagccgcggt aatacgtagg tggcaagcgt tgtcccggat ttattgggcg taaagcgagc      540
gcaggcggtt ttttaagtct gat                                              563
```

```
<210> SEQ ID NO 6
<211> LENGTH: 562
<212> TYPE: DNA
<213> ORGANISM: Lactobacillus plantarum
<220> FEATURE:
<221> NAME/KEY: misc_feature
<223> OTHER INFORMATION: Lactobacillus plantarum strain TL1

<400> SEQUENCE: 6
acgaactctg gtattgattg gtgcttgcat catgatttac atttgagtga gtggcgaact      60
ggtgagtaac acgtgggaaa cctgcccaga agcgggggat aacacctgga aacagatgct     120
aataccgcat aacaacttgg accgcatggt ccgagtttga aagatggctt cggctatcac     180
ttttggatgg tcccgcggcg tattagctag atggtggggt aacggctcac catggcaatg     240
atacgtagcc gacctgagag ggtaatcggc cacattggga ctgagacacg gcccaaactc     300
ctacgggagg cagcagtagg gaatcttcca caatggacga aagtctgatg gagcaacgcc     360
gcgtgagtga agaagggttt cggctcgtaa aactctgttg ttaaagaaga acatatctga     420
gagtaactgt tcaggtattg acggtattta accagaaagc cacggctaac tacgtgccag     480
cagccgcggt aatacgtagg tggcaagcgt tgtccggatt tattgggcgt aaagcgagcg     540
caggcggttt tttaagtctg at                                              562
```